(12) United States Patent
Riley et al.

(10) Patent No.: US 8,421,019 B2
(45) Date of Patent: Apr. 16, 2013

(54) IDENTIFICATION OF IMMUNOGLOBULIN (LG) DISORDERS USING FOURIER TRANSFORM INFRARED SPECTROSCOPY

(75) Inventors: Christopher B. Riley, Ten Mile House (CA); J. Trenton McClure, Charlottetown (CA); R. Anthony Shaw, Winnipeg (CA)

(73) Assignees: University of Prince Edward Island, Charlottetown (CA); National Research Council of Canada, Ottawa (CA)

( * ) Notice: Subject to any disclaimer, the term of this patent is extended or adjusted under 35 U.S.C. 154(b) by 1142 days.

(21) Appl. No.: 12/175,022

(22) Filed: Jul. 17, 2008

(65) Prior Publication Data
US 2010/0012844 A1    Jan. 21, 2010

(51) Int. Cl.
*G01J 5/02* (2006.01)
(52) U.S. Cl.
USPC .................................................. 250/339.08
(58) Field of Classification Search ........... 250/339.08
See application file for complete search history.

(56) References Cited

U.S. PATENT DOCUMENTS 8,124,415 B2 *   2/2012   Liu et al. ..................... 436/71

OTHER PUBLICATIONS

Budinova et al., Application of Molecular Spectroscopy in the Mid-Infrared Region to the Determination of Glucose and Cholesteral in whole blood and Blood Serum, 1997, Applied Spectroscopy, vol. 51, pp. 631-635.*

Deleris, et al., Applications of FTIR spectrometry to plasma contents analysis and monitoring, 2003, Vibrational Spectroscopy, vol. 32, pp. 129-136.*
Riley et al., Use of Fourier-Transform Infrared Spectroscopy for the Diagnosis of Failure of Transfer of Passive Immunity and Measurement of Immunoglobulin Concentrations in Horses, Jun. 28, 2008, J Vet Intern Med, vol. 21, pp. 828-834.*
Dubois et al., "IR spectroscopy's sensitivity to molecular structure and interactions provides a "molecular fingerprint", which is the basis for biomedical applications", Analytical Chemistry, Oct. 1, 2004, pp. 361A-367A.
Duarte et al., "Use of Near-Infrared Raman Spectroscopy to Detect lgG and lgM Antibodies Against Toxoplasma Gondii in Serum Samples of Domestic Cats", Cellular and Molecular Biology, vol. 48, No. 5, Sep. 25, 2001, pp. 585-589.
Shaw et al., "Infrared Spectroscopy in Clinical and Diagnostic Analysis", Encyclopedia of Analytical Chemistry, 2000, pp. 1-20.
Nikulin et al., "Near-optimal region selection for feature space reduction: novel preprocessing methods for classifying MR spectra", NMR in Biomedicine, vol. 11, 1998, pp. 209-216.
Shaw et al., "Multianalyte serum analysis using mid-infrared spectroscopy", Ann Clin Biochem, 998;35, pp. 624-632.

(Continued)

*Primary Examiner* — Christine Sung
(74) *Attorney, Agent, or Firm* — David S. Resnick; Nixon & Peabody LLP

(57) ABSTRACT

A method and a corresponding system for obtaining a serum mid-infrared spectroscopic profile using Fourier-transform infrared spectroscopy (FTIR) are described. The method comprises acquiring FTIR spectra for dried sera and preprocessing the FTIR spectra of sera by differentiation and smoothing to enhance weak spectral features and to remove baseline variations. The preprocessed FTIR spectra are normalized to a common intensity range, the normalization being performed in a spectral sub-region defined by strongest infrared (IR) absorption for a protein to obtain the serum spectroscopic profile. The serum spectroscopic profiles provide a basis to diagnose immunoglobulin disorders or to quantify serum immunoglobulin levels.

25 Claims, 10 Drawing Sheets

OTHER PUBLICATIONS

Benezzeddine-Boussaidi et al., Clin Chem Lab Med, 47:83-90 (2009). "Validation for quantification of immunoglobulins by Fourier transform infrared spectrometry."

Heise et al., Appl Spectrosc, 48:85-95 (1994). "Multicomponent assay for blood substrates in human plasma by mid-infrared spectroscopy and its evaluation for clinical analysis."

Petibois et al., Clinical Chemistry, 47, 730-738 (2001). "Plasma protein contents determined by Fourier-transform infrared spectrometry."

Shaw et al., Ann Clin Biochem, 35, 624-632 (1998). "Multianalyte serum analysis using mid-infrared spectroscopy."

* cited by examiner

IDENTIFICATION OF IMMUNOGLOBULIN (LG) DISORDERS USING FOURIER TRANSFORM INFRARED SPECTROSCOPY

FIELD OF THE INVENTION

The present invention relates generally to diagnosis of immunoglobulin (Ig) disorders. More particularly, the present invention relates to diagnosis of Ig disorders using Fourier transform infrared spectroscopy.

BACKGROUND OF THE INVENTION

Immunoglobulins (Ig) or antibodies are glycoprotein molecules that are produced by a type of white blood cells called B cells. These molecules are used by a host's immune system to identify and neutralize foreign objects, such as bacteria, viruses, and other pathogens. In placental mammals, there are five types of immunoglobulins, viz., IgA, IgD, IgE, IgG, and IgM that differ in their biological properties, functional locations and ability to respond to specific antigens.

Naïve B cells that have never been exposed to an antigen express only IgM. Mature B cells express both IgM and IgD; the co-expression of both IgM and IgD renders the B cells ready to respond to an antigen. When a cell bound antibody engages with an antigen, the B cells divide and differentiate into an antibody-producing cell called plasma cell or activated B cell. Certain activated B cells are capable of producing all five types of immunoglobulins, including IgE, IgA and IgG that have defined roles in the immune system.

Amongst the different types of immunoglobulins, IgG is the most predominant immunoglobulin in serum (about 75%) and is also the major immunoglobulin in extravascular spaces. IgG provides the majority of antibody-based immunity against invading pathogens. IgG is also the only class of immunoglobulin capable of crossing the placenta to give passive immunity to fetus.

The measurement of levels of individual types of immunoglobulins present in serum of a patient provides an antibody profile of the patient that can be used for diagnostic purposes. A deviation from a normally expected immunoglobulin level serves as an indication of a particular immunoglobulin disorder. For example, IgG levels increase in most infections such as chronic granulomatous infections; hyperimmunizations; liver diseases; severe malnutrition; dysprotenemia; hypersensitivity granulomas; dermatologic disorders; IgG myeloma; rheumatoid arthritis etc. On the other hand, IgG levels decrease in conditions such as agammaglobulimia; lymphoid aplasia; selective IgG and IgA deficiencies; IgA myeloma; Bence Jones proteinemia, chronic lymphoblastic leukemia etc.

Several tests are commonly used for the measurement of immunoglobulin concentrations in general and IgG in particular. For example, radial immunodiffusion assay (RID) is considered the gold standard test for quantitative measurement of IgG. In addition, enzyme-linked immunosorbent assays (ELISA) have been used as screening tests that measure the IgG concentration with a species-specific anti-IgG antibody. Other tests, such as the glutaraldehyde coagulation test, calorimetric assay, zinc sulfate turbidity measurements, tubimetric immunoassay, lateral flow immunoassay etc., can also be used, but these are non-specific since they detect other serum proteins in addition to immunoglobulins. These tests are primarily screening tests and hence have good sensitivity (comparable with RID), but have limited specificity.

While the RID assay provides quantitative IgG data, it requires 18-24 h to obtain results, requires more technical skill that the alternatives, is not amenable to automation, and is often more expensive than the alternatives.

It is, therefore, desirable to provide a rapid test for diagnosis of immunoglobulin disorders that is both highly sensitive and highly specific.

SUMMARY OF THE INVENTION

In a first aspect, there is provided a method for obtaining a serum mid-infrared spectroscopic profile using Fourier-transform infrared spectroscopy (FTIR). The method comprises acquiring FTIR spectra for dried sera and preprocessing the FTIR spectra by differentiation and smoothing to enhance weak spectral features and to remove baseline variations. The preprocessed FTIR spectra are normalized to a common intensity range, the normalization being performed in a spectral sub-region defined by strongest infrared (IR) absorption for a protein to obtain the serum spectroscopic profile for providing a basis to diagnose immunoglobulin disorders or to quantify serum immunoglobulin levels.

In an embodiment, the strongest infrared absorption corresponds to the protein amide I band envelope.

In a further embodiment, the method further comprises identifying, in the serum spectroscopic profile, spectroscopic features conveying diagnostic information of interest using pattern recognition models. An immunoglobulin disorder is then diagnosed using the diagnostic information.

In another embodiment, the method further comprises quantifying the serum immunoglobulin levels using quantification models on the serum spectroscopic profile.

In a further aspect, there is provided a system for obtaining a serum mid-infrared spectroscopic profile using Fourier-transform infrared spectroscopy (FTIR). The system comprises a FTIR spectrometer, a preprocessing module, a normalization module, and a user interface. The FTIR spectrometer is used for obtaining FTIR spectra for dried sera. The preprocessing module preprocesses the FTIR spectra by differentiation and smoothing to enhance weak spectral features and to remove baseline variations. The normalization module normalizes the preprocessed FTIR spectra to a common intensity range. The normalization is performed in a spectral sub-region defined by strongest infrared (IR) absorption for a protein to obtain the serum spectroscopic profile and provides a basis to diagnose immunoglobulin disorders or to quantify serum immunoglobulin levels. The user interface displays the diagnosis or serum immunoglobulin levels.

In an embodiment, the system further comprises a pattern recognition module for identifying, in the serum spectroscopic profile, spectroscopic features conveying diagnostic information of interest using pattern recognition models and a diagnostic module for diagnosing an immunoglobulin disorder using the diagnostic information.

In a further embodiment, the system further comprises a quantification module for quantifying the serum immunoglobulin levels using quantification models on the serum spectroscopic profile.

In a further aspect, there is provided a machine-readable medium containing sets of instructions, code sequences, configuration information, or other data, which, when executed, cause a processor to perform steps in a method a method for obtaining a serum mid-infrared spectroscopic profile using Fourier-transform infrared spectroscopy (FTIR). The method comprises acquiring FTIR spectra for dried sera and preprocessing the FTIR spectra by differentiation and smoothing to enhance weak spectral features and to remove baseline variations. The preprocessed FTIR spectra are normalized to a common intensity range, the normalization being performed in a spectral sub-region defined by strongest infrared (IR) absorption for a protein to obtain the serum spectroscopic profile for providing a basis to diagnose immunoglobulin disorders or to quantify serum immunoglobulin levels.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Infrared (IR) spectroscopy is a quantitative and qualitative technique, which can be used for diagnostic characterization of biological molecules in fluids and tissues. Infrared radiation is transmitted through the sample of interest, and the IR spectrometer records the wavelength dependence of radiation absorption by the sample. Simple, small molecules yield simple spectra with well-resolved absorption bands that reflect both their chemical structure and concentration. In complex samples the number and size of molecular species both increases, causing the number of absorption bands and the extent of band overlap to increase. The spectra reflect both the structure of the individual IR active constituents and their relative abundance. The absorption patterns within the IR spectra of biological samples may be viewed as biochemical fingerprints that provide a basis for the quantitative determination of various serum and urine analytes of diagnostic interest.

The spectroscopic signatures of serum proteins are more similar than different. The dominant spectroscopic features arising from proteins reflect the features common to them, for instance, the amide linkages. Thus, quantitative and qualitative measurements of serum proteins using IR spectra present a unique challenge, particularly in cases where the protein of interest (for example, IgG) is present at a concentration substantially lower than the aggregate concentration of other serum proteins. The spectroscopic differences are so small that commonly used methods would reasonably be expected to fail in the attempt to develop accurate quantitative assays for individual, minor proteins. Not only are the differences among the spectra of individual proteins very subtle—they are further masked by sample to sample variations in the concentrations of minor serum components (e.g. glucose, urea, cholesterol, and other minor proteins) so that even diligent application of the known quantitative and qualitative techniques would not be guaranteed of success.

Thus, in order to develop accurate diagnostic tests, the infrared spectra need to be judiciously preprocessed, after they are collected, but before the application of quantitative and qualitative analysis.

Generally, there is provided a method and system for the diagnosis of immunoglobulin disorders by applying diagnostic classification models (such as, classification algorithms) on processed infrared spectra (FTIR spectra) to identify diagnostically relevant features. Alternatively, the processed infrared spectra can be used to directly quantify an analyte concentration in sera through the use of quantification models (such as, partial least squares).

Figure 1:
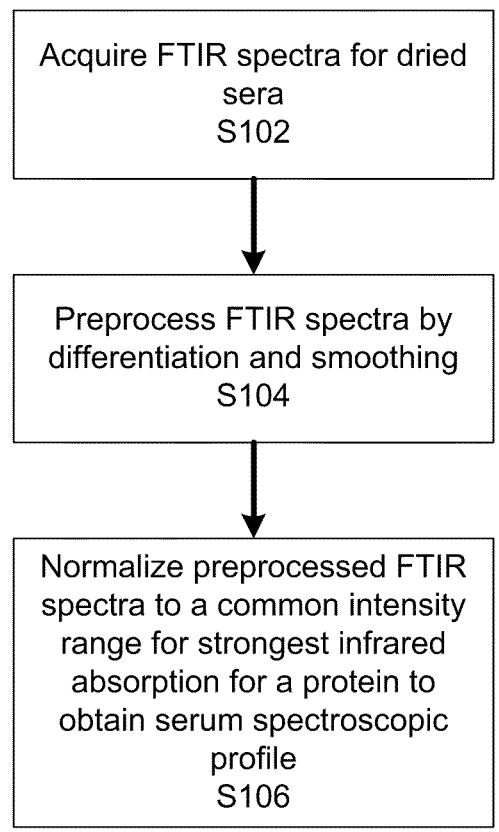
FIG. 1 is a flow diagram illustrating a method for obtaining a serum mid-infrared spectroscopic profile using Fourier-transform infrared spectroscopy (FTIR) according to an aspect.

Specifically, there is provided a method for obtaining a serum mid-infrared spectroscopic profile using Fourier-transform infrared spectroscopy (FTIR) as shown in FIG. 1. The method comprises acquiring FTIR spectra for dried sera (Step S102) and preprocessing the FTIR spectra by differentiation and smoothing to enhance weak spectral features and to remove baseline variations (Step S104). The preprocessed FTIR spectra are normalized to a common intensity range, the normalization being performed in a spectral sub-region defined by strongest infrared (IR) absorption for a protein to obtain the serum spectroscopic profile (Step S106). The serum spectroscopic profiles provide a basis to diagnose immunoglobulin disorders or to quantify serum immunoglobulin levels.

Figure 2:
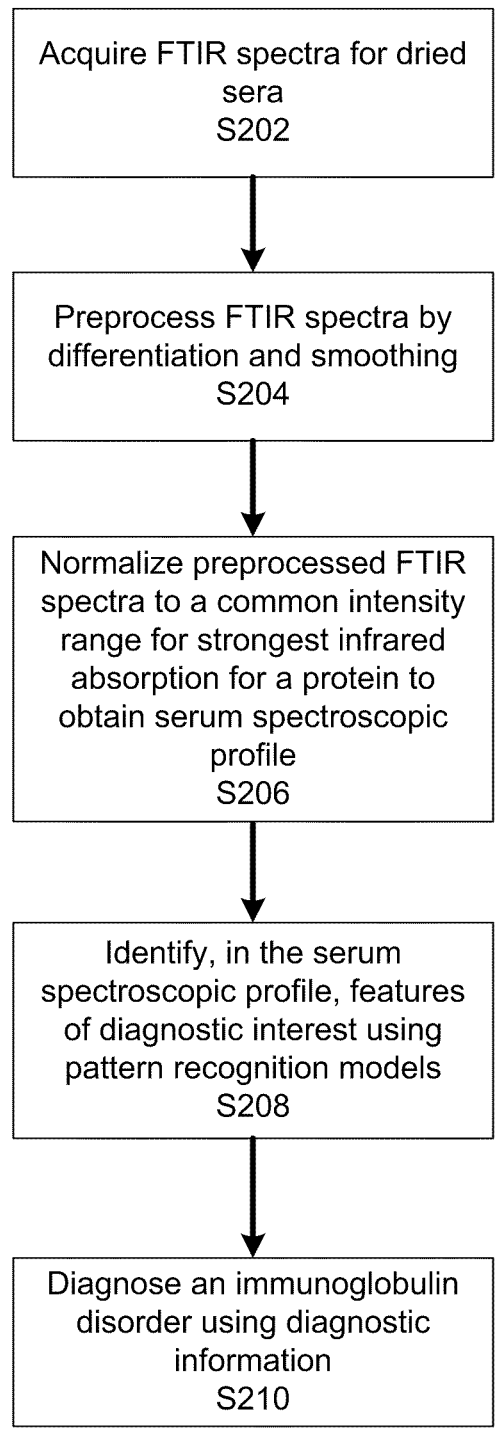
FIG. 2 is a flow diagram illustrating a method for diagnosis of immunoglobulin disorders according to an embodiment.

Furthermore, according to an embodiment, there is provided a method of diagnosis of immunoglobulin disorders using Fourier-transform infrared spectroscopy (FTIR). The method comprises, as shown in FIG. 2, acquiring an FTIR spectra for dried sera (Step S202) and preprocessing the FTIR spectra by differentiation and smoothing to enhance weak spectral features and to remove baseline variations (Step S204). The preprocessed FTIR spectra are normalized to a common intensity range in a spectral sub-region defined by strongest infrared (IR) absorption for a protein to obtain serum spectroscopic profile (Step S206). Spectroscopic features conveying diagnostic information of interest are identified, in the serum spectroscopic profile, using pattern recognition models (Step S208). An immunoglobulin disorder can then be diagnosed using the diagnostic information (Step S210).

Figure 3:
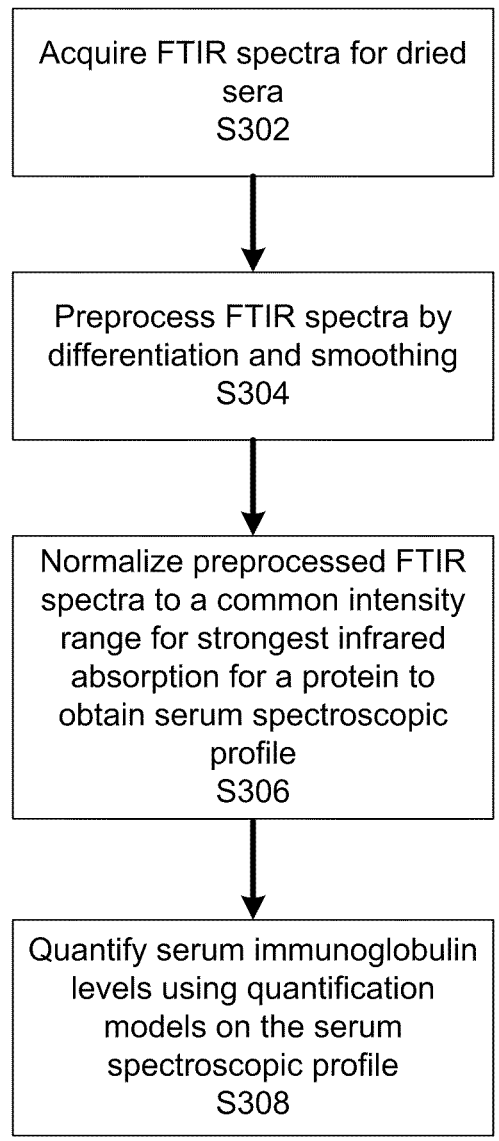
FIG. 3 is a flow diagram illustrating a method for quantification of an analyte in sera according to another embodiment.

Additionally, according to another embodiment, there is provided a method of quantification of immunoglobulin levels in sera using FTIR. The method comprises, as shown in FIG. 3, acquiring an FTIR spectra for dried sera (Step S302); preprocessing FTIR spectra by differentiation and smoothing to enhance weak spectral features and to remove baseline variations (Step S304). The preprocessed FTIR spectra are normalized to a common intensity range in a spectral sub-region defined by strongest IR absorption for a protein to obtain serum spectroscopic profile (Step S306). The serum immunoglobulin levels can be determined directly from the serum spectroscopic profile using quantification models (Step S308).

Figure 4:
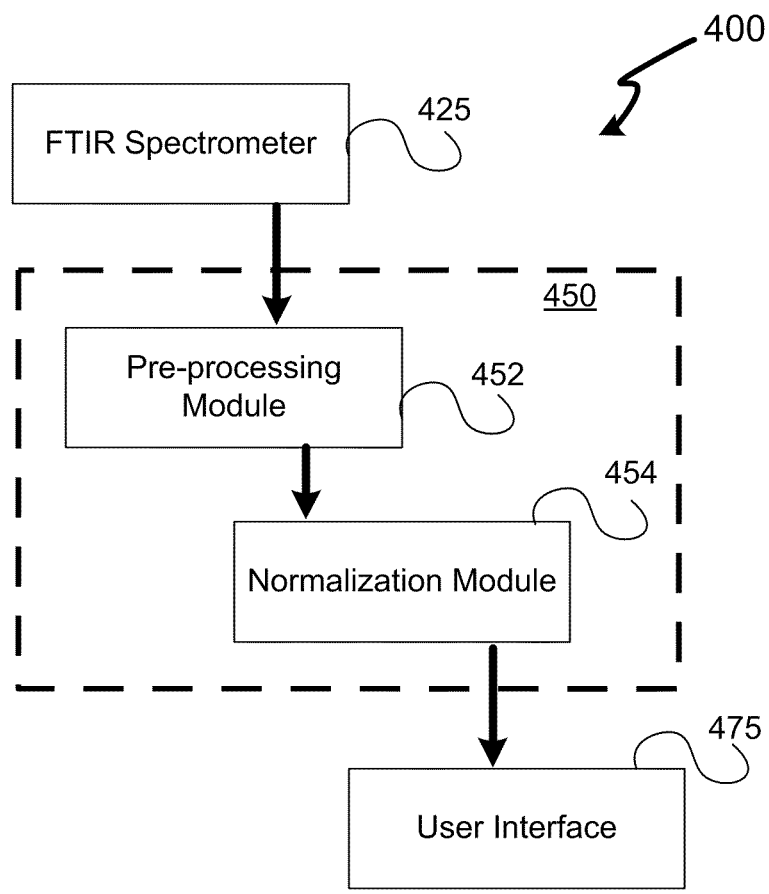
FIG. 4 is a schematic diagram illustrating a system for obtaining a serum mid-infrared spectroscopic profile using Fourier-transform infrared spectroscopy (FTIR) according to an aspect.

In accordance with an aspect, there is provided a system 400 for obtaining a serum mid-infrared spectroscopic profile using FTIR, as shown in FIG. 4. The system comprises a FTIR spectrometer 425, an execution block 450 including a preprocessing module 452 and a normalization module 454, and a user interface 475. The FTIR spectrometer 425 is used for obtaining FTIR spectra for dried sera. The preprocessing module 452 preprocesses the FTIR spectra by differentiation and smoothing to enhance weak spectral features and to remove baseline variations. The normalization module 454 normalizes the preprocessed FTIR spectra to a common intensity range. The normalization is performed in a spectral sub-region defined by strongest infrared (IR) absorption for a protein to obtain the serum spectroscopic profile and provides a basis to diagnose immunoglobulin disorders or to quantify serum immunoglobulin levels. The user interface 475 displays the diagnosis or serum immunoglobulin levels.

Figure 5:
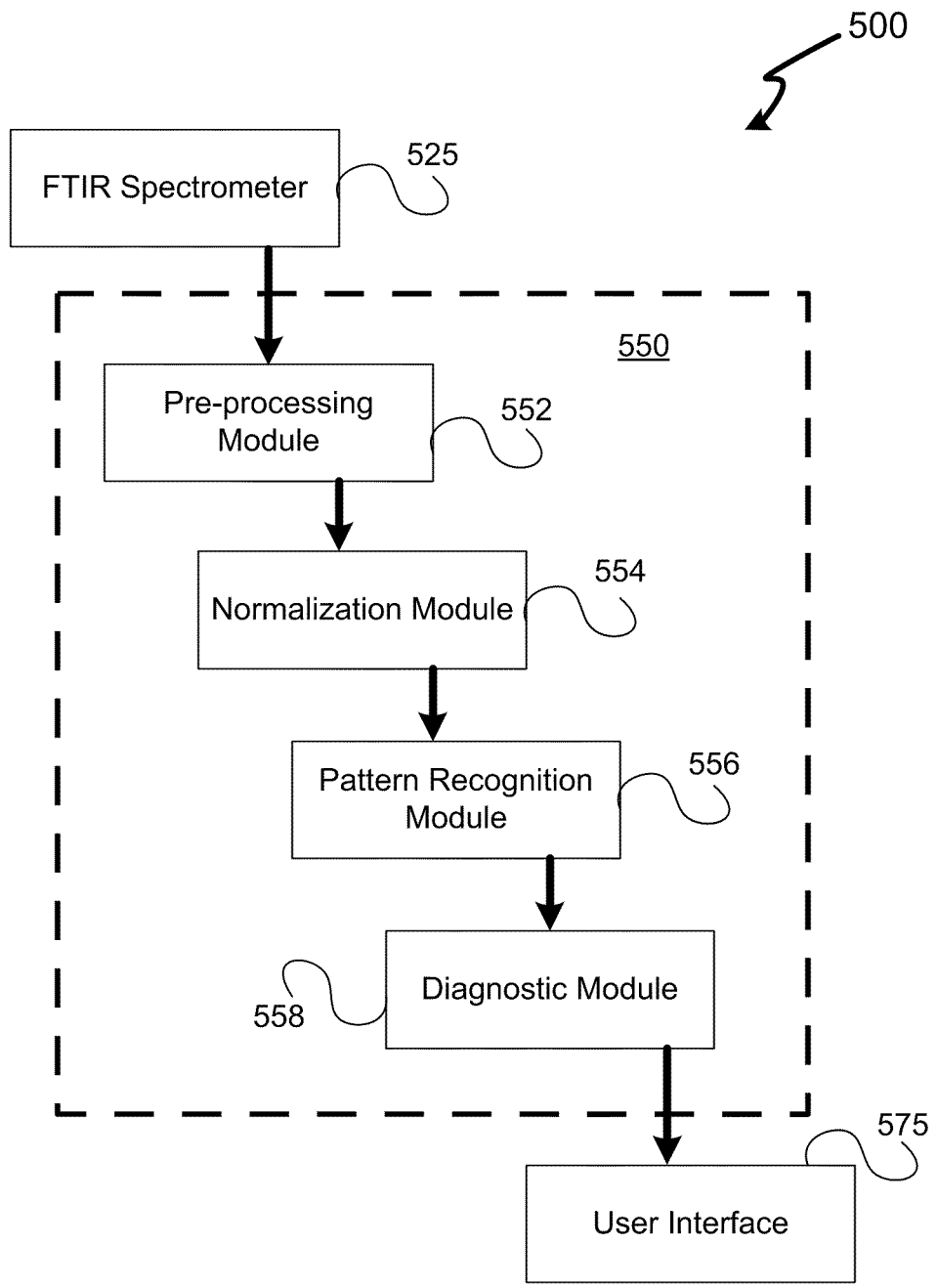
FIG. 5 is a schematic diagram illustrating a system for diagnosis of immunoglobulin disorders according to an embodiment.

An embodiment of the system 500 for diagnosis of immunoglobulin disorders using FTIR is shown in FIG. 5. A FTIR spectrometer 525 is used to collect FTIR spectra from samples of interest, for example, dried sera. The FTIR spectra are then processed by the execution block 550 for obtaining diagnostic information on immunoglobulin disorders. The FTIR spectra are pre-processed, by a pre-processing module 552, by differentiation and smoothing to enhance weak spectral features and to remove baseline variations. The normalization module 554 normalizes the preprocessed FTIR spectra to a common intensity range in a spectral sub-region defined by strongest infrared (IR) absorption for a protein to obtain serum spectroscopic profile. Pattern recognition module 556 identifies spectroscopic features conveying diagnostic information of interest, in the serum spectroscopic profile, using pattern recognition models. The diagnostic module 558 diagnoses an immunoglobulin disorder using the diagnostic information, which can then be displayed using the user interface 575.

Figure 6:
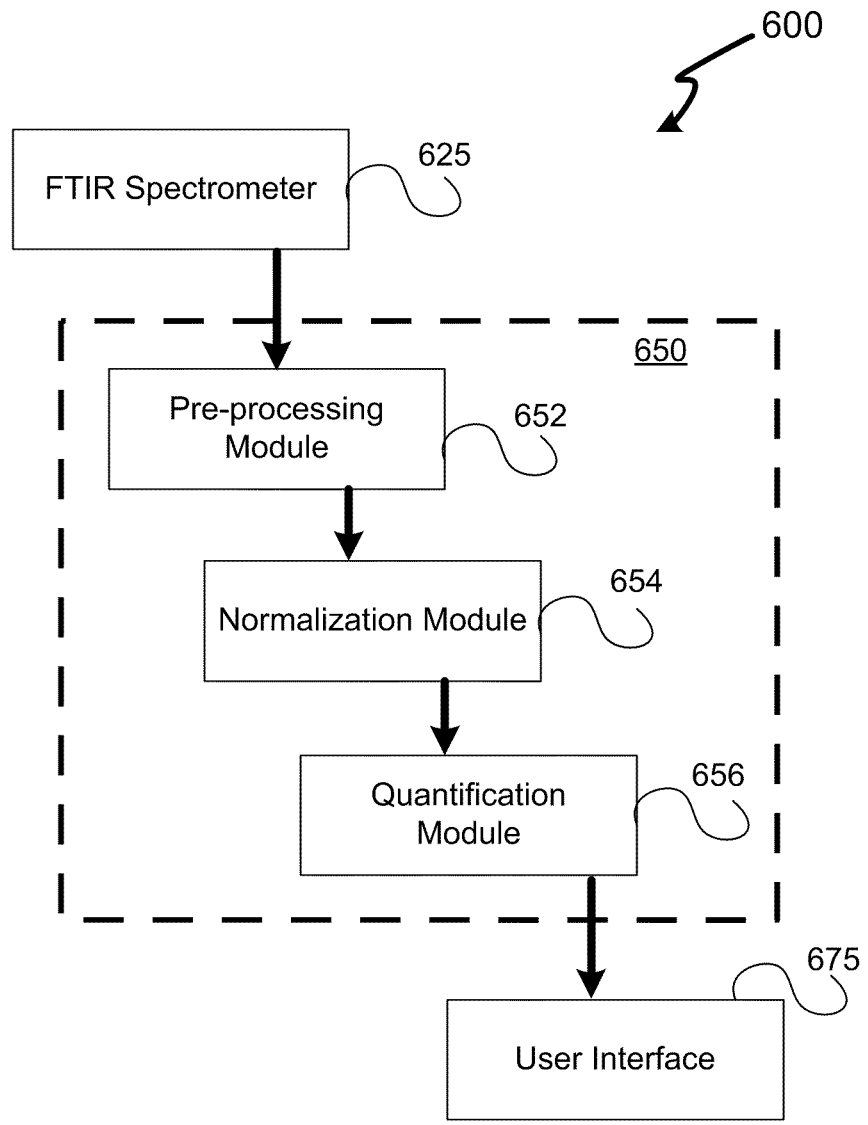
FIG. 6 is a schematic diagram illustrating a system for quantification of an analyte in sera according to another embodiment.

As shown in FIG. 6, an embodiment of the system 600 for quantification of immunoglobulin levels in sera is similar to the system 500 of FIG. 5. A FTIR spectrometer 625 is used to collect FTIR spectra from samples of interest, for example, dried sera. The FTIR spectra are then processed by the execution block 650 for obtaining quantitative information of immunoglobulin levels in sera. The FTIR spectra are pre-processed, by a pre-processing module 652, by differentiation and smoothing to enhance weak spectral features and to remove baseline variations. The normalization module 654 normalizes the preprocessed FTIR spectra to a common intensity range in a spectral sub-region defined by strongest infrared (IR) absorption for a protein to obtain serum spectroscopic profile. Quantification module 656 determines serum immunoglobulin levels directly from the serum spectroscopic profile using quantification models, which can then be displayed using the user interface 675. The immunoglobulin levels thus determined could be used for diagnostic purposes.

Typically, spectroscopic data are preprocessed by differentiation and smoothing procedures to enhance weak spectral features and to remove baseline variations using spectral manipulation software. For example, differentiation and smoothing can be performed using Savitsky Golay $2^{nd}$ order derivatives using $2^{nd}$ degree polynomial functions as described in Adams, M J, Feature selection and extraction; in: Barnett NW, ed. Chemometrics in Analytical Spectroscopy, Cambridge, UK: Royal Society of Chemistry; 2004: 55-99.

The preprocessing step is followed by a normalization step to normalize the spectra to a common metric. Commonly used techniques for normalization include normalizing to a common overall intensity in all spectra or to normalize using an internal standard.

Normalizing to a common overall intensity involves the normalization of all spectra in the data set to a common integrated intensity across the entire range of observed absorptions, i.e., across the entire measured spectral range. In cases where derivative spectra are used, the integration also accounts for the possibility of positive and negative intensities by using "vector normalization". In the vector normalization procedure, the spectra are scaled such that the dot product of the vector of spectroscopic intensities with itself is equal to unity, i.e. the "length" of the vector of spectroscopic intensities is unity.

In the internal standard normalization procedure, all of the specimens are spiked with a compound (for example, potassium thiocyanate) that serves as an internal standard, by virtue of a prominent spectroscopic feature well removed from the features characteristic of biological samples. By spiking all samples to a common concentration in this internal standard, all spectra can be normalized to a common effective optical path length. The aim of this procedure is to compensate for imprecision in the preparation of the dry films used for obtaining the spectra. A practical benefit of the internal standard normalization procedure is that the quantitative information is more accurately reflected in the spectra; spectral intensities more faithfully reproduce the sample-to-sample differences in absolute concentrations for the various specimens in the sample set.

However, neither normalizing to a common overall intensity in all spectra or the internal standard normalization procedure yield satisfactory results in cases where the protein of interest (for example, Ig) is present at a concentration substantially lower than the aggregate concentration of other serum proteins.

Thus, the preprocessed FTIR spectroscopic data need to be normalized in manner so as to provide meaningful information on analytes present at low concentrations prior to the application of quantitative and qualitative analysis models.

Figure 8:
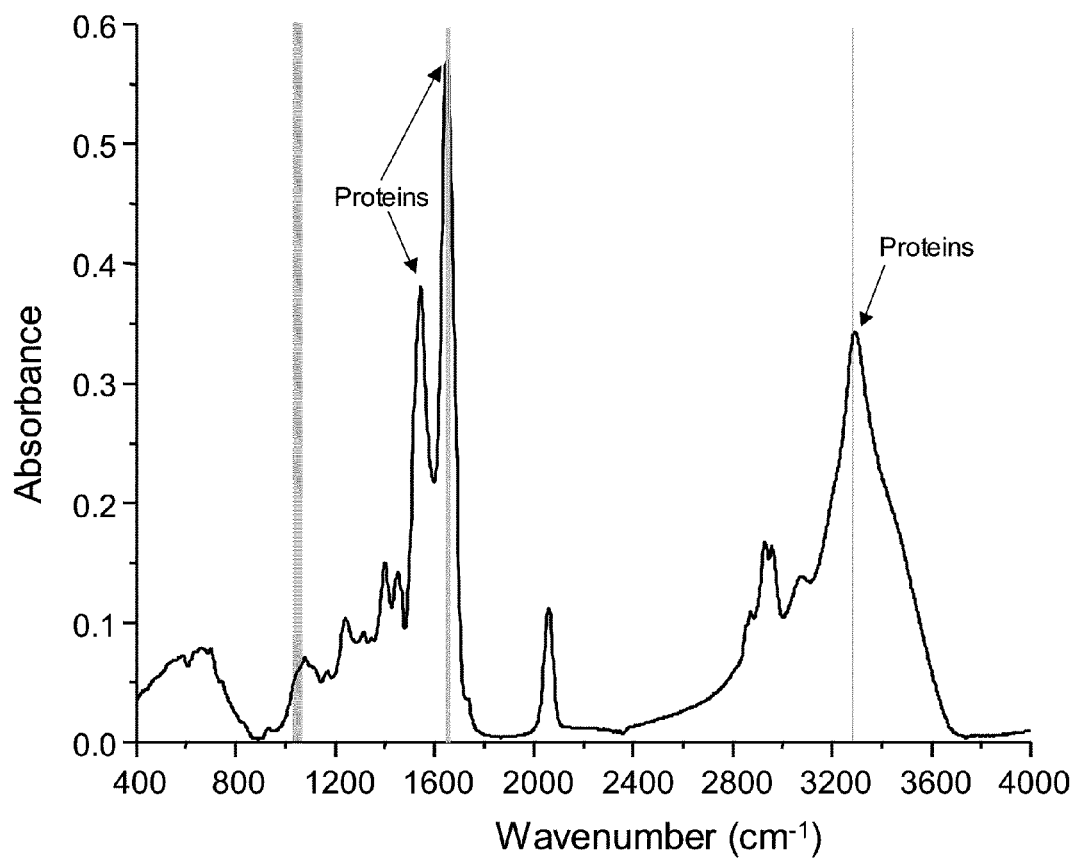
FIG. 8 is a representative infrared spectrum of foal serum.

According to an aspect, this is achieved by subjecting the preprocessed infrared spectra to vector normalization wherein all spectra are normalized to a common intensity range in a spectral sub-region defined by strongest protein absorption (for example, see FIG. 8). The common intensity range for normalization is preferably 1600-1800 $cm^{-1}$ and more preferably 1620-1680 $cm^{-1}$. The absorption band encompasses the "amide I" band, which lies in the 1620-1680 $cm^{-1}$.

Using the above normalization range, the variations in overall protein concentrations may be factored out, thus generating normalized spectra that optimally reflect the spectroscopic distinctions that arise from the differences in the concentrations of individual proteins. In particular, the large sample-to-sample variations in the spectral intensity arising from sample-to-sample fluctuations in overall protein concentration are factored out. Eliminating or minimizing the large variations accentuates subtle sample-to-sample spectroscopic variations due to differences in the relative abundance of different serum proteins.

It is to be noted that neither of the commonly used normalization procedures discussed earlier, viz.; the full-spectrum normalization procedure (normalization to a common overall intensity) and the internal standard normalization method yield satisfactory results for diagnostic measurements of immunoglobulins (accuracy levels of less than 80%). Neither of these methods could eliminate nor minimize the large sample-to-sample variations in the spectral intensity arising from sample-to-sample fluctuations in overall protein concentration. Normalization to the overall spectral intensity ensured that the collective spectroscopic contributions of all constituents—including proteins and all other serum constituents—were rendered identical (on average). Normalization to an internal standard preserved (as it is expected to preserve) the sample-to-sample variations in absolute intensity corresponding to sample-to-sample variations in protein concentration. Thus, the commonly used normalization procedures did not result in a data set suited for further processing in the identification of immunoglobulin disorders.

The preprocessed infrared spectra, normalized to a common intensity range in a spectral sub-region defined by strongest protein absorption, can be used for both diagnostic and quantitative analysis.

For diagnostic analysis, a pattern recognition technique is used to seek specific spectral ranges within which the spectra differed systematically for normal specimens and those having immunoglobulin related disorders. The pattern recognition model is optimized using classification algorithms, for example, genetic optimal region selection algorithm (GA-ORS) in a training set and validated by predicting status in test sets. The GA-ORS algorithm is used, for example, as described in Nikulin A E, Dolenko B, Bezabeh T, Somorjai R L; Near-optimal region selection for feature space reduction: novel preprocessing methods for classifying MR spectra; NMR Biomed 1998; 11:209-216.

For quantitative analysis, the preprocessed spectroscopic data is converted to quantitative analytical information using partial least squares (PLS) multivariate techniques. A calibration model PLS quantification algorithm is optimized using least-square relationships among the training set and corresponding RID data (current gold standard test). The optimized model is further validated by the model's ability to predict analyte concentrations on the basis of spectra in the test sets. The multivariate technique, is used, for example, as described in Khattree R, Naik D N; Discrimnant analysis; in: Multivariate Data Reduction and Discrimination with SAS Software; Cray, N.C.: SAS Institute Inc; 2002:211-345; and Beebe K R, Kowalski B R; An introduction to multivariate calibration and analysis; Anal Chem 1987; 59:1007A-1017A.

The method and system described herein can be used for the diagnosis of a number of immunoglobulin disorders. For example, the method and system described herein can be used for the diagnosis of failure of passive transfer of immunity (FPT) and identification of mares at risk of producing foals with FPT. Additionally, the method can be used for the other immunoglobulin disorders such as hypo-gammaglobulinemia; hyper-gammaglobulinemia; severe combined immunodeficiency; HIV associated diseases; plasma cell myeloma; lymphoma, and diseases that result in immunoglobulin imbalance. Furthermore, the method can be used for the diagnosis of immunoglobulin disorders characterized by an increase or decrease in immunoglobulin levels and to generate antibody profiles of patients or subjects of interest.

Table 1 summarizes a number of disorders characterized by increased levels of immunoglobulins IgM, IgA, IgD, and IgE:

| Disorder | Characterized by an increase in: |
| --- | --- |
| Waldenström's macroglobulinemia | IgM |
| Trypanosomiasis | IgM |
| Actinomycosis | IgM |
| Carrión's disease (bartonellosis) | IgM |
| Malaria | IgM |
| Infectious mononucleosis | IgM |
| Lupus erythematosus | IgM |
| Rheumatoid arthritis | IgM |
| Dysgammaglobulinemia (certain cases) | IgM |
| Wiskott-Aldrich syndrome | IgA |
| Cirrhosis of the liver (most cases) | IgA |
| Certain stages of collagen and other autoimmune disorders such as rheumatoid arthritis and lupus erythematosus | IgA |
| Chronic infections not based on immunologic deficiencies | IgA |
| IgA myeloma | IgA |
| Chronic infections | IgD |
| IgD myelomas | IgD |
| Atopic skin diseases such as eczema | IgE |
| Hay fever | IgE |
| Asthma | IgE |
| Anaphylactic shock | IgE |
| IgE-myeloma | IgE |

Table 2 summarizes a number of disorders related to decreased levels of immunoglobulins IgM, IgA, and IgE:

| Disorder | Characterized by an decrease in: |
| --- | --- |
| Agammaglobulinemia | IgM |
| Lymphoproliferative disorders (certain cases) | IgM |
| Lymphoid aplasia | IgM, IgA |
| IgG and IgA myeloma | IgM |
| Dysgammaglobulinemia | IgM |
| Chronic lymphoblastic leukemia | IgM, IgA |
| Hereditary ataxia telangiectasia | IgA |
| Immunologic deficiency states (e.g., dysgammaglobulinemia, agammaglobulinemia, and hypogammaglobulinemia) | IgA |
| Malabsorption syndromes | IgA |
| IgG myeloma | IgA |
| Acute lymphoblastic leukemia | IgA |
| Congenital agammaglobulinemia | IgE |
| Hypogammaglobulinemia due to faulty metabolism or synthesis of immunoglobulins | IgE |

The application of embodiments will now be described with respect to specific examples of the use of Fourier-transform infrared spectroscopy for the diagnosis of failure of passive transfer of immunity (FPT) in horses and the identification of mares at risk of producing foals diagnosed with FPT. Although the specific examples pertain to disorders related to IgG, the methods and systems described herein can be applied to the diagnosis of immunoglobulin disorders arising from other types of immunoglobulin.

EXAMPLE 1

Diagnosis of FPT

As described earlier, immunoglobulins are present in the serum and other tissue fluid of mammals, consisting primarily of IgG. In the immuno-competent animal, IgG is synthesized by plasma cells following the activation of lymphocytes by antigenic stimulation. Deficiency of IgG may be congenital or acquired, and has been associated with an increased susceptibility to bacterial, viral or fungal infection in humans and animals. Many neonatal mammals are immunologically immature and rely upon the passive transfer of maternal antibodies via the placenta or the colostrum, depending upon the type of placentation in a particular species. In humans, placentation is haemendothelial, and therefore, IgG is transferred to the fetus in-utero. In dogs and cats, endothelochorial placentation results in a 5-10% in-utero transfer of IgG to the neonate, with the remainder being provided in the colostrum. Animals with syndesmochorial (ruminants) or epitheliochorial (horses and camelids) placentation are born severely hypogammaglobulinemic (characterized by reduced levels of all types of gamma globulins), and rely upon colostrum intake to confer early humoral immunity and to prevent microbial infection. In these species, the successful transfer of colostrum from the mother to the newborn offspring is a critical contributor to neonatal survival. Insufficient maternal antibody absorption by the neonate results in a condition is called failure of passive transfer (FPT).

Neonates with FPT have a greatly increased risk of morbidity and mortality that can best be prevented by early diagnosis and therapeutic intervention. The condition is uncommon in human infants, but reported prevalence in domestic animals is 20% in camelids, up to 35% in cattle, and 3-20% in horses. The economic and accurate screening of foals and other neonates for FPT is essential to ensure timely medical intervention, and to minimize morbidity, mortality and financial loss. Consequently many tests have been developed for the diagnosis of FPT, and are widely used in the equine, and to a lesser degree, in bovine and other species.

FPT is typically diagnosed using quantitative measurements of IgG in neonatal serum. The majority of neonatal foals have serum IgG concentrations greater than 1000 mg/dL following the intestinal absorption of colostrum, with those less than 400 mg/dL being classified as having FPT, and those with levels between 800 and 400 mg/dL as having partial FPT. Neonates with FPT have an increased risk of morbidity and mortality due to septicemia (blood poisoning), requiring early diagnosis of FPT and appropriate medical intervention. The reference range for normal foal IgG values is generally established using radial immunodiffusion assay (RID), which is considered the gold standard test for quantitative measurement of IgG.

Samples

Sera obtained previously and stored at −80° C. were used. The samples had been collected from foals (predominantly Standardbred) of the Maritime Provinces of Canada according to a protocol approved by the Animal Care Committee of the University of Prince Edward Island. Foals (N=194), 24-72 h of age, had blood collected to quantify serum IgG levels as part of a routine post-partum foal examination. Blood was allowed to clot, and the serum was separated and stored in a −80° C. freezer until all tests could be performed. An equine RID IgG test was used as the gold standard test to determine each foal's serum IgG concentrations. Each serum sample was tested in duplicate, and the average of the results used to determine IgG concentration. Sera with IgG concentrations in excess of 1600 mg/dL (the RID manufacturer's stated upper testing limit) were diluted to fall within the performance range of the assay. ELISA tests as well as a noncommercial glutaraldehyde coagulation test were also performed on these sera.

Fourier-Transform Infrared Spectroscopy

Sera (N=194) were thawed at 20° C. and vortexed. For each sample, an aliquot was drawn and diluted in 4 g/L potassium thiocyanate solution in the ratio 1 part serum:1 part KSCN solution. Duplicate dry films were made for each sample by applying 8 μL aliquots of the diluted serum, spread evenly in circular motion onto 5 mm wells within a custom made, adhesive masked, 96-well, silicon microplate. Once the films were thoroughly dried (12 h at 20° C.), the microplate was mounted within a multisampler interfaced with a FTIR spectrometer equipped with a deuterium tryglycine sulfate detector to allow for the acquisition of IR spectra. Absorbance spectra in the IR range of 400-4000 $cm^{-1}$ were recorded. For each acquisition, 512 interferograms were signal averaged and Fourier transformed to generate a spectrum with a nominal resolution of 4 $cm^{-1}$.

Data Preprocessing

Differentiation and smoothing procedures (Savitsky-Golay $2^{nd}$ order derivatives using $2^{nd}$ degree polynomial functions, with 9 point smoothing) were performed on all spectra to resolve and enhance weak spectral features and to remove baseline variations using spectral manipulation software (GRAMS/Al 7.02, Thermo Galactic, Salem, N.H.). The spectra were then normalized by using a vector normalization script written in MatLab™; the $2^{nd}$ derivative spectra were scaled by calculating for each spectrum the square root of the sum of square intensities over the wavenumber range of 1600-1800 $cm^{-1}$, and then dividing that spectrum by this factor. With this procedure completed, all spectra had the same integrated intensity (unity) within the specified range encompassing the strongest IR absorption (for example, the protein amide I band envelope used here). These normalized spectra then provided the basis to develop both quantitative and qualitative diagnostic tests as described below.

Diagnostic and Analytical Test Development

The 194 sera samples were divided into 2 categories: IgG concentrations less than 400 mg/dL (FPT positive) and greater than 400 mg/dL (FPT negative). This resulted in an overweighing of the FPT negative group, which could create challenges in pattern recognition or regression methods in the development phase of IR spectroscopy. To circumvent that possibility, samples with IgG concentrations greater than 1600 mg/dL were excluded from the initial dataset used to train both the pattern recognition (diagnostic) and regression (quantification) methods. Moreover, any method optimized to distinguish FPT positive from FPT negative samples in the IgG range of 0-1600 mg/dL would correctly classify those spectra/samples with values greater than 1600 mg/dL as FPT-negative; the latter were therefore considered only during the validation phase of the study.

Diagnostic FPT test. A pattern recognition technique was used to identify spectroscopic features conveying the diagnostic information of interest. In particular, a genetic "optimal region selection" (ORS) algorithm was utilized to seek specific spectral ranges within which the spectra differed systematically for FPT (IgG less than 400 mg/dL) versus non-FPT (IgG greater than 400 mg/dL) foals. The samples with IgG levels less than 1600 mg/dL were split into a training set and a separate, independent test set including 92 (26 FPT and 66 negative) and 47 (14 FPT and 33 negative) samples respectively, with their counterpart RID-IgG values. The choice of diagnostic spectral sub-regions was optimized through ORS trials using the training set only as input, and using linear discriminant analysis as the basis to partition the spectra into FPT and non-FPT groups. The optimization procedure resulted in a diagnostic classifier that took preprocessed IR spectra as input and provided FPT status as output, for both the training and test sets. Finally, the optimal diagnostic classifier was implemented to predict FPT status for each of the test samples with IgG levels greater than 1600 mg/dL; a posteriori comparison to the RID diagnoses further validated the diagnostic classifier.

The sensitivity (Se) and specificity (Sp) for the IR based test were calculated using the RID IgG values as the gold standard. Positive (PPV) and negative (NPV) predictive values were calculated at the average reported FPT prevalence (P) in the literature, and compared to the same values for other equine FPT tests either directly, or as calculated from previously published Se and Sp data. The relevant formulae were:

$$PPV = Se \times P / ([Se \times P] + [(1-Sp) \times (1-P)])$$

$$NPV = Sp \times (1-P) / ([Sp \times (1-P)] + [(1-Se) \times P])$$

Infrared based quantitative IgG assay. A quantitative assay for IgG was developed using a multivariate partial least squares (PLS) technique. All PLS trials used preprocessed spectra that were split into training and test sets identical to those employed for the diagnostic classification model; of the two separate test sets, one encompassed 47 samples (14 FPT and 33 negative) that spanned the 0-1600 mg/dL IgG range, and the second included all 55 samples (110 spectra) with IgG levels greater than 1600 mg/dL. The PLS calibration model to convert spectroscopic to quantitative analytical information was derived by optimizing least-squares relationships between the spectra and corresponding RID derived IgG levels in the training set only. The PLS quantification algorithm was then validated by its ability to predict IgG concentrations on the basis of spectra in the independent test sets.

Results

Figure 7:
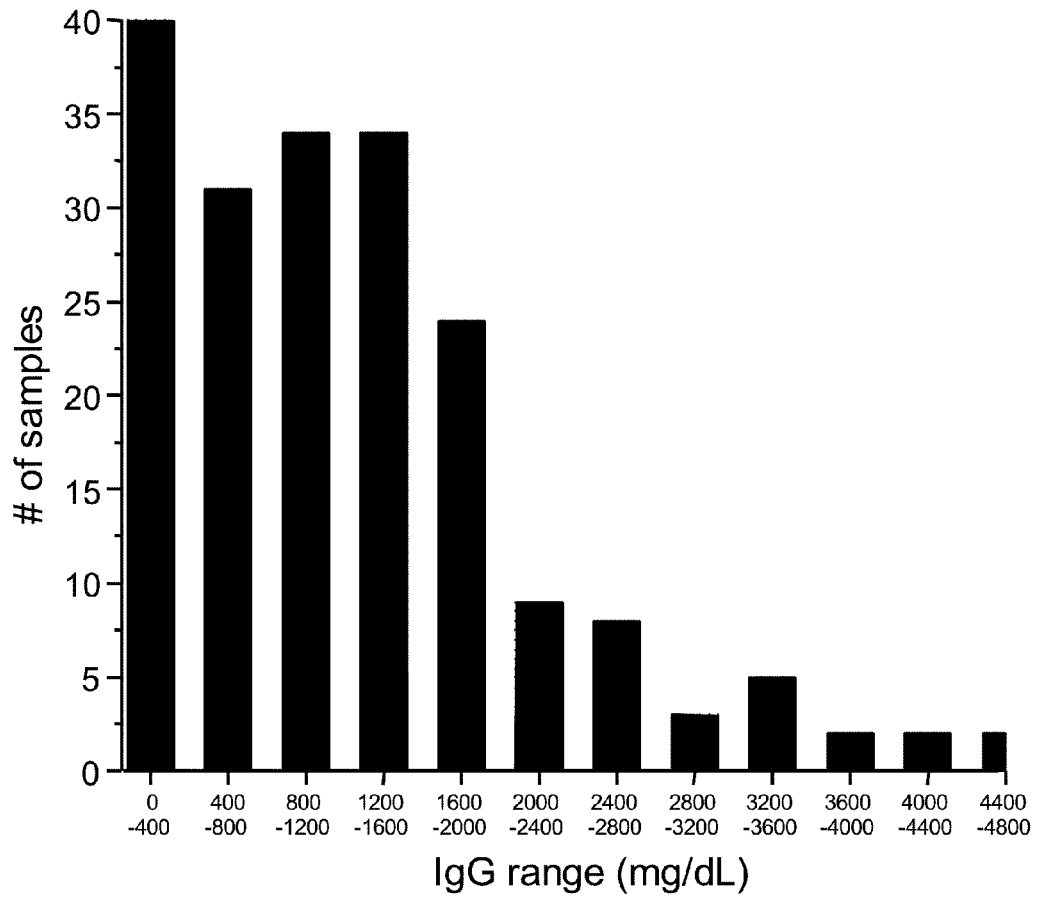
FIG. 7 is a histogram illustrating the frequency of occurrence of foal samples (N=194) having IgG concentrations within the ranges as indicated determined by RID assay.

For the 194 samples the RID IgG levels ranged from less than 200 mg/dL to greater than 4700 mg/dL as shown in FIG. 7. FIG. 7 is a histogram illustrating the frequency of occurrence of foal samples having (RID assay-determined) IgG concentrations within the ranges indicated (N=194). Forty samples had IgG levels below the 400 mg/dL cut-off diagnostic of FPT, while 154 were FPT-negative; 55 of these had values greater than 1600 mg/dL. The prevalence of FPT for the whole data set was 20.6%. To illustrate the nature of the measurements, a representative IR spectrum is plotted in FIG. 8. The most intense features arise from proteins: bands centered at 1650 cm$^{-1}$ (amide 1) and 1545 cm$^{-1}$ (amide 11) correspond to stretching and bending vibrations localized on the amide C=O and N—H groups, respectively; the broad band at ~3300 cm$^{-1}$ also corresponds to the N—H group, but is a stretching vibration termed the amide A mode. Highlighted within FIG. 8 are three spectral regions identified by the ORS algorithm as optimal to distinguish the spectra of serum from FPT versus non-FPT foals. Based upon the spectroscopic information within these discriminatory sub-regions, the IR spectra provided the FPT status with a success rate of 95%. Significantly, this accuracy was maintained for both the training set of spectra (used to identify the optimal sub-regions) and the independent test set. When the 55 samples with IgG values greater than 1600 mg/dL were included in the test set, the validation set classification accuracy was 97%. Classification tables, specificity, sensitivity, accuracy and predictive values are summarized in Table 3.

Figure 9:
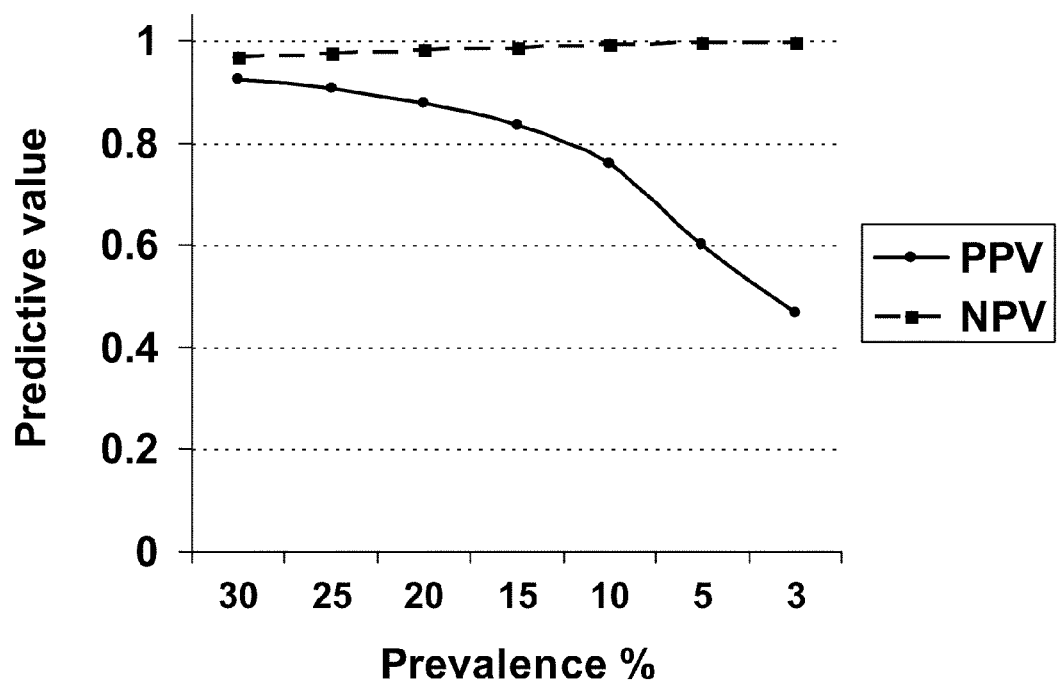
FIG. 9 is a plot of positive (PPV) and negative (NPV) predictive values versus prevalence for infrared-based diagnosis of FPT in foal in accordance with an embodiment.

The variations in PPV and NPV for the IR based test over the reported range of prevalence are illustrated in FIG. 9. The Se, Sp, accuracy, PPV and NPV are compared to their counterparts for other FPT diagnostic tests (from previously published reports) in Table 4. The positive and negative predictive values in Table 4 are based on a FPT prevalence of 15%, which is the average prevalence from previous reports.

Figure 10:
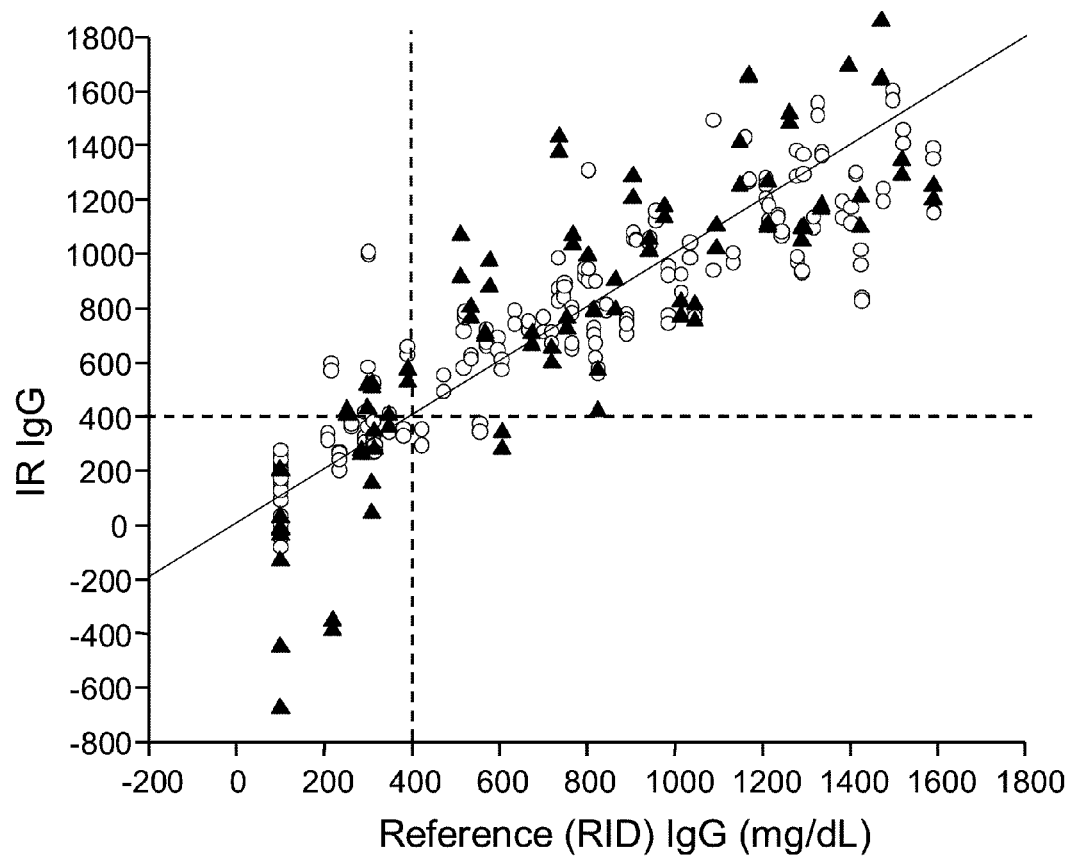
FIG. 10 is a scatterplot comparing serum IgG concentrations as determined by infrared-based diagnosis of FPT in foal in accordance with an embodiment to RID assay data.

The accuracy of the PLS quantification algorithm is summarized by the scatterplots within FIG. 10, which compare the IgG levels as provided by RID (the current gold standard) to their counterparts as determined using the IR spectroscopy-based method described herein. In FIG. 10, the open circles denote the 184 training spectra (92 samples), whereas the triangles represent set of 94 independent test spectra (47 samples). The line of identity and guidelines at the 400 mg/dL level are included for reference. Note that for samples with IgG concentrations less than 200 mg/dL, the RID assay did not provide quantitative information. These scatterplots show comparable or in some cases better accuracy for the training and test sets with correlation coefficients for RID versus IR spectroscopy based IgG concentrations of 0.90 and 0.86 for training and test sets respectively. The optimal PLS calibration model included nine PLS factors, using two spectral ranges, 700-1710 cm$^{-1}$ and 2750-3500 cm$^{-1}$, that encompassed all of the major absorptions.

Moreover, although the RID assays are typically reported with 3-4 significant digits (for example, 821 mg/dL, 1041 mg/dL etc.), the last 2 digits are not significant. The actual measurements comprise estimating the diameters in zones of inhibition (in mm, with a naked eye or mild magnification) and then converting these measurements to quantitative estimates of IgG concentrations through a linear regression model developed from four standards zones of inhibition. Uncertainties in these measurements translate to uncertainty in the derived IgG concentrations. Therefore, the reported RID values would be more consistent with the actual assay's accuracy if the results were reported as +/−50 mg/dL. In other words, if the RID calculated value, for example is 821 mg/dL, the actual concentration is as likely to be 770 or 880 mg/dL as it is 821 mg/dL. Thus, this limitation of the RID poses a problem when it is used as a gold standard to develop and evaluate the accuracy of another test. For example, when the serum IgG value is close to one of the "cut off" values set for IgG deficiency in FPT and other IgG disorders, apparent "misclassification" (in the case of diagnostic testing) or "inaccuracy" (in the case of a quantitative assay) may in fact be due to the limited accuracy of the gold standard RID assay. When the current FTIR method very closely matches the IgG levels provided RID (as is the case here), the possibility exists that the current FTIR method is in fact more accurate than RID.

TABLE 3

Classification table for calibration, validation and combined data sets comparing radial immunodiffusion to infrared spectroscopy:

| Infrared-based diagnosis | Radial immunodiffusion[1] | | | | | | | |
|---|---|---|---|---|---|---|---|---|
| | IgG < 400 mg/dl | IgG > 400 mg/dl | Total | Se % | Sp % | Accuracy % | PPV % | NPV % |
| Calibration data | | | | | | | | |
| Ig < 400 mg/dl | 48* | 5 | 53 | | | | | |
| Ig > 400 mg/dl | 4 | 127* | 131 | 92.3 | 96.2 | 95.1 | 86.3 | 98.0 |
| Total | 52 | 132 | 184 | | | | | |

TABLE 3-continued

Classification table for calibration, validation and combined data sets comparing radial immunodiffusion to infrared spectroscopy:

| Infrared-based diagnosis | Radial immunodiffusion[1] | | Total | Se % | Sp % | Accuracy % | PPV % | NPV % |
|---|---|---|---|---|---|---|---|---|
| | IgG < 400 mg/dl | IgG > 400 mg/dl | | | | | | |
| Validation data[2] | | | | | | | | |
| Ig < 400 mg/dl | 26* | 2 | 28 | | | | | |
| Ig > 400 mg/dl | 2 | 64* | 66 | 92.9 | 97.0 | 95.7 | 88.8 | 98.1 |
| Total Validation data[3] | 28 | 66 | 94 | | | | | |
| Ig < 400 mg/dl | 26* | 5 | 31 | | | | | |
| Ig > 400 mg/dl | 2 | 171* | 173 | 92.9 | 97.2 | 96.6 | 89.5 | 98.1 |
| Total Combined data | 28 | 176 | 204 | | | | | |
| Ig < 400 mg/dl | 74* | 10 | 84 | | | | | |
| Ig > 400 mg/dl | 6 | 298* | 304 | 92.5 | 96.8 | 95.9 | 88.1 | 98.0 |
| Total | 80 | 308 | 388 | | | | | |

[1]Sp = specificity; Se = sensitivity;
PPV = positive predictive value = ratio of true positives over sum of true and false positives;
NPV = negative predictive value = ratio of true negatives over sum of true and false negatives.
PPV and NPV calculations based on study prevalence of 20.6%.
[2]Validation data including only samples with IgG levels in the range 0-1600 mg/dL.
[3]Validation data as above, but also including all samples with IgG levels greater than 1600 mg/dL.
*Number of samples that were correctly classified.

TABLE 4

Comparison of recently evaluated tests for failure of passive transfer (IgG < 400 mg/ml) with prevalence = 15%

| Diagnostic test | Se % | Sp % | Acc % | PPV % | NPV % | Source of assay |
|---|---|---|---|---|---|---|
| Infrared | 92.5 | 96.8 | 95.9 | 83.4 | 98.7 | |
| Glutaraldehyde coagulation | 95 | 80 | | 72.8 | 95.7 | In-house |
| Zinc sulphate turbidity | 88.9 | 79.4 | 82 | 43.2 | 97.6ᶜ | EquiZ equine FPT test kit, VMRD Inc., Pullman, WA 99163 |
| | 89 | 91 | | 63.6 | 97.9 | In-house |
| | 94 | 83 | | 49.4 | 98.7 | In house - refractometry |
| | 94 | 72 | | 37.2 | 98.6 | In house - visual method |
| Turbimetric immunoassay | 63 | 92 | 88.1 | 58.1 | 93.4 | In-house |
| ELISA A | 88.9 | 78.1 | 81 | 41.7 | 97.5 | Midland 4, Plasma Foal IgG Quick test kits, Midland Bioproducts Corp., Boone, IA 50036 |
| ELISA B | 76 | 95 | 81 | 58.2 | 93.4 | SNAP ® foal IgG, Idexx laboratories, Westbrook, ME 04092 |
| | 88.9 | 95.8 | 93.4 | 78.9 | 95.8 | |
| | 90 | 79 | | 43.1 | 97.8 | |
| Colorimetric immunoassay | 100 | 96 | 97 | 81.5 | 100 | DVM Stat., VDx Inc., Belgium, WI 53004 |

The above example demonstrates that the IR spectra of serum can be used for the diagnosis of FPT. This may be accomplished either by means of diagnostic classification of the processed spectra, or through the use of a quantification method (in the present case, PLS) to quantify IgG levels directly from the spectra. Both procedures are validated by their ability to accurately characterize large, independent sets of test samples.

The diagnostic accuracy of the IR based test meets or surpasses currently available alternatives (see Table 4), and the methodology carries several practical advantages. For example, hemoglobin (from possible hemolysis) and other chemical interferents may compromise the accuracy of some testing modalities. In the present approach, such interferents are accounted for by ensuring that the spectral dataset used to develop the diagnostic algorithms encompasses the full range of possible interferents, "inoculating" them against the possibility of chemical interference. Since no reagents are required, the per-test cost can be very low and repeat testing is inexpensive. No standards need to be prepared before testing, and results are available within minutes. Samples were allowed to dry for 12 h in the present study for convenience so a large number of samples could be run at once. In practice, however, samples dried within a few minutes and IR spectroscopy may be performed immediately after the sample is dry. As an added benefit unique to this testing modality, the same spectrum can in principle provide simultaneously results for the serum total protein, albumin, cholesterol, glucose, triglyceride and urea concentrations at no additional cost. Finally, in common with RID, zinc sulphate turbidity, and calorimetric assays, the IR test can also quantify IgG concentrations.

A significant advantage of having the quantitative assay to complement the diagnostic algorithm is that borderline cases may be identified as such. To illustrate, the scatterplot is divided into quadrants categorizing each of the IR spectroscopy based assays as true positive, true negative, false positive (FP), or false negative (FN) (see FIG. 8). Clearly, the majority of cases were designated correctly by the IR-based assay. Where the IR and RID designations disagree (FN and FP quadrants), most samples fall close to 400 mg/dL with none of the FP sera having an RID IgG value greater than 800 mg/dL and only 2 FN sera having an IR IgG value greater than 800 mg/dL. The simultaneous quantitative and qualitative IR assessment of sera minimizes the need for confirmatory testing. Of particular interest are cases for which IgG levels exceed 400 mg/dL, but considered suboptimal (less than 800 mg/dL). Foal IgG management for such cases may be guided by knowledge of an accurate IgG concentration, in concert with other factors.

The PPV and NPV values vary with the population prevalence of FPT, which must therefore be considered when using this test. The population studied here was predominantly Standardbred foals in Atlantic Canada, and the prevalence of FPT was similar to that previously reported for Standardbred foals. In populations where the prevalence of FPT is low, it is suggested that foals found to have FPT may require verification by accessing the quantitative IR based IgG value or via another confirmatory test.

The overall performance (accuracy) of the IR based test described herein was similar to that of the calorimetric assay, and superior to other tests currently available. The sensitivity was superior to that of ELISA and turbimetric assays, similar to that of glutaraldehyde coagulation and zinc sulphate assays, and lower than that of the calorimetric assay. Specificity was similar to that attained by calorimetric assay, but superior compared to published results for all other assays. The NPV is high, as is the case for most of the other testing modalities. The most obvious distinguishing feature of the IR based approach is the high PPV, which was superior to that reported for other tests. A high PPV has been difficult to achieve in the diagnosis of FPT, and is of particular importance in reducing the unnecessary and expensive treatment of otherwise healthy neonates.

Although accurate enough to be considered the gold standard in FPT testing, recent work has shown that RID assays may vary, depending upon the standards used to establish the concentration curve, and typical turnaround times are 18-24 h. As a consequence, it has been proposed that universal standards for the RID assays be used. Although the glutaraldehyde coagulation is fast and inexpensive, it has been reported to have generally poor or variable specificity, especially for IgG concentrations less than 800 mg/dL, thus prompting confirmatory testing to verify a positive test result. Hemolysis may result in false positive results for both the zinc sulphate turbidity and glutaraldehyde coagulation assays. While the ELISA based tests offer the convenience of onsite testing, they have a poorer PPV as compared to the IR test, and involve the use of heat and contamination sensitive reagents. The ELISA tests are also among the more expensive options, which decreases their appeal for screening large numbers of animals. An economic comparison of different test for FPT suggests that the cost per test varied from $US 2.00 to 13.65, with the cost of some tests varying depending upon the number of samples tested at any one time (e.g. RID).

The IR based test is reagent free (no kit is required), standards are not required, and it is estimated that currently each test costs less than US$ 1 per sample, irrespective of the number of samples to be evaluated.

While the diagnostic method described herein focused on the 400 mg/dL IgG level as the FPT cut-off point in order to allow ready comparison with other published methods, the methodology would be readily adapted or interpreted to further distinguish between FPT and partial FPT (IgG greater than 400 mg/dL and less than 800 mg/dL). Introduced in the mid 1980's, the term "partial FPT" does not, on its own, indicate the need for IgG supportive therapy, however values within this range are considered clinically significant in clinically ill foals. While the significance in clinically normal foals remains controversial, many clinicians regard foals with concentrations less than 800 mg/dl as candidates for IgG supplementation therapy.

EXAMPLE 2

Identification of Mares at Risk of Producing Foals with FPT

Although indirect assessment of mares at risk of producing foals diagnosed with FPT have been reported, a reliable and accurate method and system for the identification of mares at risk is not available. The indirect assessment methods include estimation of the specific gravity of colostrum and by measurement of colostrum IgG concentrations. In addition, other mare-related factors reported to adversely affect the quality of colostrum include premature lactation or parturition, prolonged gestation, dystocia, age, parity, breed, season of foaling and poor mothering behavior.

In normal mares relationships between serum total protein and IgG concentrations, and parturition and colostrogenesis have been found, but there is no method or system available for the identification of mares at risk of producing FPT-positive foals.

The application of embodiments will now be described with respect to a specific example of the use of Fourier-transform infrared spectroscopy for the identification of mares at risk of producing foals diagnosed with FPT.

Samples

Sera obtained during a previous study of FPT in foals were used. Blood samples were collected from post-parturient Standardbred mares (N=126) and their foals (N=126) according to a protocol approved by the Animal Care Committee of the University of Prince Edward Island. Foals 24-72 h of age and their dams, had blood collected to quantify foal serum IgG levels as part of a routine post-partum foal examination. Blood was allowed to clot, and the serum was separated and stored in a −80° C. freezer until all tests could be performed. An equine RID IgG test was used as the gold standard test to determine each foal's serum IgG concentrations. For the RID IgG testing, each serum sample was tested in duplicate, and the average of the results used to determine IgG concentration. Sera with IgG concentrations in excess of the RID manufacturer's stated upper testing limit were serially diluted to fall within the performance range of the assay. The IgG concentrations of foals born to risk-positive mares ranged from below the detectable limit of the RID IgG assay (200 mg/dL) to 422 mg/dL, and for those born to risk-negative mares from 511 mg/dL to 4762 mg/dL (mean 1597 mg/dL).

Fourier-transform Infrared Spectroscopy and Data Preprocessing

FTIR spectral data and preprocessing of the infrared spectra were performed as previously described under Example 1.

Diagnostic at-risk Evaluation Test

A pattern recognition technique was used to identify spectroscopic features conveying the diagnostic information of interest. In particular, a genetic algorithm-based "optimal region selector" (GA-ORS) was used to seek specific spectral ranges within which the groups of spectra differed systematically. The mare sera samples were divided into two categories based on the equine RID IgG test results for their corresponding foals. Spectra from mares whose foals had IgG concentrations less than 422 mg/dL (N=42 spectra; 21 mares) were assigned to the risk-positive class, and mares whose foals had IgG concentrations greater than 511 mg/dL (N=210 spectra; 105 mares) to the risk-negative class for the purpose of the study. The interval between 422 mg/dL and 511 mg/dL, where no samples were available, formed a natural separation between the 2 groups. The spectral data within the 700-1700 cm-1 range were evaluated for classification features capable of distinguishing between the risk-positive and risk-negative mares, using the ORS to reduce the spectral data to a few wavenumber regions of interest. The GA-ORS region selection procedure used linear discriminant analysis (LDA) as the "wrapper" classifier, with leave-one-out (LOO) cross-validation ("wrapper" means that a classifier is used to select optimal discriminatory sub-regions, based on classification accuracy). For this procedure, the dataset was split randomly into training and test sets (50% of the risk-positive and 50% of the risk-negative spectra were put in each set), and as described above, feature selection was carried out on the training set. Once the optimally discriminatory regions were found, the test set was used to validate the classifier. To compensate for the 1:5 ratio of risk positive to risk negative spectra, misclassification of risk positive samples was penalized five times more in the LDA calculations than misclassification of risk negative spectra.

The small size of the risk-positive dataset necessitated a refinement to the approach described above. Although the algorithm was restricted to seek only 4 (or fewer) regions, any classifier based upon a single 50:50 data split would inevitably be less than optimal simply because any single GA-ORS trial would only include 20-22 spectra (10-11 samples) for the risk positive group. To compensate for the deficiency inherent to this "single split" approach, the GA-ORS procedure was repeated 50 times, for 50 different training/test data splits. The 50 different "optimal" sets of spectral regions were then combined into a histogram reporting the frequency with which each data point on the wavenumber axis was included within the set of optimal regions. This histogram clearly highlighted three spectral regions as playing the most important roles. The final classifier was therefore built upon the averages of the three regions encompassing points that appeared in more than 40% of the GA-ORS trials.

Upon identification of the optimal regions, the ultimate LDA classifier was then computed by using a bootstrap-based cross-validation method to improve robustness. For example, as described in Efron B and Tibshirani R J; An Introduction to the Bootstrap; Chapman and Hall, New York, N.Y. 1993. As previously for the feature selection, the data were split randomly into training set (15 risk-positive and 15 risk negative samples) and test set (6 risk-positive and 90 risk-negative). The best LDA classifier for that split was then determined by LDA of the training data, with the LDA coefficients then serving to predict classifications for the test data for that split. To ensure robustness, this process was repeated 10,000 times with 10,000 different training/test splits. A weighted average of the LDA coefficients of the 10,000 classifiers, with weight proportional to the accuracies on the test sets, was used to obtain the final set of coefficients. The result of this procedure was a diagnostic classifier that took a pre-processed IR spectrum as input, and provided as the output the mare's risk status that could be compared, a posteriori to the true FPT status of their foals.

The sensitivity (Se) and specificity (Sp) of IR spectroscopy to detect risk-positive mare sera were calculated using the corresponding foal RID IgG values as the gold standard reference. Positive (PPV) and negative (NPV) predictive values were calculated based on the study prevalence (P) for FPT of 16.67% and prevalence values from previous reports.

Results

Based upon the IR spectroscopic information within three discriminatory sub-regions identified by the algorithms (970-993 $cm^{-1}$, 1369-1386 $cm^{-1}$, and 1425-1450 $cm^{-1}$), the IR spectra provided the risk status of the mares with a classification success rate of 73.0%. The sensitivity of the classification system was 76.2% (16 of 21 risk-positive samples correctly classified) and specificity was 72.4% (76 of 105 risk-negative samples correctly classified). At a study foal-FPT prevalence of 16.67%, PPV and NPV were 35.6% and 93.8% respectively.

Thus, it has been demonstrated that the IR spectra of mare serum specimens may provide the basis for a screening method for mares at risk of having a foal susceptible to FPT. Although many previous reports on FPT allude to mare-associated risk factors for FPT, few have objectively evaluated the statistical significance of such factors or used statistical modeling for their identification. In one study, only season at time foaling was clearly associated, but a second identified the age of the mare, breed, and duration of gestation period, to be statistically significant risk factors for decreased IgG concentration in colostrum, and therefore FPT. Furthermore, premature lactation has been identified as another statistically significant factor for FPT.

In the current example, non-IR-based risk factors were not specifically identified and pre-selected for inclusion in model development. Such information was unavailable for the samples used. Although non-inclusion of other factors would help the FTIR diagnostic method as a stand-alone objective measure of the risk of a mare having a FPT positive foal, inclusion of other reported factors in conjunction with IR spectral features might enhance the performance of the method and system described herein.

In summary, the method and system described herein provide for the diagnosis of a number of immunoglobulin disorders. For example, the method and system described herein can be used for the diagnosis of failure of passive transfer of immunity (FPT) and identification of mares at risk of producing foals with FPT using Fourier transform infrared spectroscopy (FTIR). Alternatively, the method and system described herein can provide quantitative information on analyte concentration in sera. For example, immunoglobulin concentration in sera can be quantified directly from FTIR spectra.

In the preceding description, for purposes of explanation, numerous details are set forth in order to provide a thorough understanding of the embodiments. However, it will be apparent to one skilled in the art that these specific details are not required in order to practice the invention.

Embodiments of the invention can be represented as a software product stored in a machine-readable medium (also referred to as a computer-readable medium, a processor-readable medium, or a computer usable medium having a computer-readable program code embodied therein). The machine-readable medium can be any suitable tangible medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment. Those of ordinary skill in the art will appreciate that other instructions and operations necessary to implement the described invention can also be stored on the machine-readable medium. Software running from the machine-readable medium can interface with circuitry to perform the described tasks.

The above-described embodiments are intended to be examples only. Alterations, modifications and variations can be effected to the particular embodiments by those of skill in the art without departing from the scope of the invention, which is defined solely by the claims appended hereto.

What is claimed is:

1. A method for obtaining a mid-infrared spectroscopic profile using Fourier-transform infrared spectroscopy (FTIR) for detecting or diagnosing immunoglobulin disorders or for quantifying immunoglobulin levels in a subject, comprising:
    acquiring FTIR spectra for at least one dried biological fluid sample;
    preprocessing the FTIR spectra by differentiation and smoothing to enhance weak spectral features and to remove baseline variations; and
    normalizing the preprocessed FTIR spectra to a common intensity range, the normalization being performed in a spectral sub-region defined by strongest infrared (IR) absorption for a protein to obtain the spectroscopic profile for providing a basis to detect or diagnose immunoglobulin disorders or to quantify immunoglobulin levels.

2. The method of claim 1, wherein the strongest IR absorption corresponds to the protein amide I band envelope.

3. The method of claim 2, wherein the spectral sub-region for normalization is 1600-1800cm$^{-1}$.

4. The method of claim 2, wherein the spectral sub-region for normalization is 1620-1680cm$^{-1}$.

5. The method of claim 1, further comprising:
    identifying, in the spectroscopic profile, spectroscopic features conveying diagnostic information of interest using pattern recognition models; and
    diagnosing an immunoglobulin disorder using the diagnostic information.

6. The method of claim 5, wherein the pattern recognition model is a genetic optimal region selection model.

7. The method of claim 5, wherein the immunoglobulin disorder is failure of passive transfer of immunity (FPT).

8. The method of claim 5, wherein the immunoglobulin disorder is an increased risk in mares of producing foals diagnosed with FPT.

9. The method of claim 5, wherein the disorder is at least one of hypogammaglobulinemia; hyper-gammaglobulinemia; and diseases that result in immunoglobulin imbalance.

10. The method of claim 1, further comprising
    quantifying the immunoglobulin levels using quantification models on the spectroscopic profile.

11. The method of claim 10, wherein the quantification model is a multivariate partial least squares model.

12. The method of claim 10, for use in detection of immunoglobulin disorders.

13. The method of claim 12, wherein the disorder is failure of passive transfer of immunity (FPT).

14. The method of claim 12, wherein the immunoglobulin disorder is an increased risk in mares of producing foals diagnosed with FPT.

15. The method of claim 12, wherein the disorder is at least one of hypogammaglobulinemia; hyper-gammaglobulinemia; and diseases that result in immunoglobulin imbalance.

16. The method of claim 1, wherein the dried biological fluid sample is dried serum, or dried colostrum from the mother of newborn offspring.

17. A system for obtaining a mid-infrared spectroscopic profile using Fourier-transform infrared spectroscopy (FTIR) for detecting or diagnosing immunoglobulin disorders or for quantifying immunoglobulin levels in a subject, comprising:
    a FTIR spectrometer for obtaining FTIR spectra for at least one dried a biological fluid sample;
    a preprocessing module for preprocessing the FTIR spectra by differentiation and smoothing to enhance weak spectral features and to remove baseline variations;
    a normalization module for normalizing the preprocessed FTIR spectra to a common intensity range, the normalization being performed in a spectral sub-region defined by strongest infrared (IR) absorption for a protein to obtain the spectroscopic profile for providing a basis to detect or diagnose immunoglobulin disorders or to quantify immunoglobulin levels; and
    a user interface for displaying results for the detection or diagnosis, or immunoglobulin levels.

18. The system of claim 17, wherein the strongest IR absorption corresponds to the protein amide I band envelope.

19. The system of claim 17, further comprising:
    a pattern recognition module for identifying, in the spectroscopic profile, spectroscopic features conveying diagnostic information of interest using pattern recognition models; and
    a diagnostic module for diagnosing an immunoglobulin disorder using the diagnostic information.

20. The system of claim 17, further comprising:
    a quantification module for quantifying the immunoglobulin levels using quantification models on the spectroscopic profile.

21. The system of claim 17, wherein the dried biological fluid sample is dried serum, or dried colostrum from the mother of newborn offspring.

22. A machine-readable medium containing sets of instructions, code sequences, configuration information, or other data, which, when executed, cause a processor to perform a method for obtaining a mid-infrared spectroscopic profile using Fourier transform infrared spectroscopy (FTIR) for detecting or diagnosing immunoglobulin disorders or for quantifying immunoglobulin levels in a subject, comprising:
    acquiring FTIR spectra for at least one dried biological fluid sample;
    preprocessing the FTIR spectra by differentiation and smoothing to enhance weak spectral features and to remove baseline variations; and
    normalizing the preprocessed FTIR spectra to a common intensity range, the normalization being performed in a spectral sub-region defined by strongest infrared (IR) absorption for a protein to obtain the spectroscopic profile for providing a basis to detect or diagnose immunoglobulin disorders or to quantify immunoglobulin levels.

23. The machine-readable medium of claim 22, wherein the method further comprises:
    identifying, in the spectroscopic profile, spectroscopic features conveying diagnostic information of interest using pattern recognition models; and
    diagnosing an immunoglobulin disorder using the diagnostic information.

24. The machine-readable medium of claim 22, wherein the method further comprises:

quantifying the immunoglobulin levels using quantification models on the spectroscopic profile.

25. The machine-readable medium of claim 22, wherein the dried biological fluid sample is dried serum, or dried colostrum from the mother of newborn offspring.

* * * * *